(12) United States Patent
Conklin

(10) Patent No.: US 6,239,254 B1
(45) Date of Patent: May 29, 2001

(54) DISULFIDE CORE POLYPEPTIDES

(75) Inventor: Darrell C. Conklin, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/326,039

(22) Filed: Jun. 4, 1999

Related U.S. Application Data

(60) Provisional application No. 60/088,136, filed on Jun. 4, 1998.

(51) Int. Cl.[7] .................................................. A16K 38/00
(52) U.S. Cl. ......................... 530/300; 435/219; 536/23.5
(58) Field of Search ............................. 435/219; 530/300

(56) References Cited

PUBLICATIONS

Tsunemi et al. Crystal Structure of an Elastase–Specific Inhibitor Elafin Complexed with Porcine Pancreatic Elastase Determined at 1.9 ç Resolution. Biochemistry. 1996, vol. 35, pp. 11570–11576.*

Incyte Pharmaceuticals Inc., No. INC319707, Aug. 25, 1995.
Marra, et al., WashU–HHMI Mouse EST Project, No. 900965, 1996.
Marra, et al., WashU–HHMI Mouse EST Project, No. 518480, 1996.
Marra, et al., WashU–HHMI Mouse EST Project, No. 895754, 1996.
Marra, et al., WashU–HHMI Mouse EST Project, No. 902108, 1996.

* cited by examiner

*Primary Examiner*—Nashaat T. Nashed
*Assistant Examiner*—Christian L. Fronda
(74) *Attorney, Agent, or Firm*—Paul G. Lunn, Esq.

(57) ABSTRACT

The present invention relates to polynucleotide and polypeptide molecules for a disulfide core protein (Zdsc1). The polypeptides, and polynucleotides encoding them, are serine proteinase inhibitors. Also disclosed are expression vectors containing polynucleotides which encode a Zdsc1 polypeptide, antibodies which specifically bind to Zdsc1 polypeptides and anti-idiotypic antibodies which neutralize the antibodies which specifically bind to Zdsc1 polypeptides.

2 Claims, No Drawings

DISULFIDE CORE POLYPEPTIDES

DISULFIDE CORE POLYPEPTIDES

The present application claims the benefit under 35 U.S.C. §119(e) of U.S. Provisional Application Serial No. 60/088,136 filed Jun. 4, 1998.

BACKGROUND OF THE INVENTION

Protein inhibitors are classified into a series of families based on extensive sequence homologies among the family members and the conservation of intrachain disulfide bridges, see Laskowski and Kato, *Ann. Rev. Biochem.* 49: 593–626 (1980). An example of a serine proteinase inhibitor is the serine proteinase inhibitor aprotinin which is used therapeutically in the treatment of acute pancreatitis, various states of shock syndrome, hyperfibrinolytic hemorrhage and myocardial infarction. Administration of aprotinin in high doses significantly reduces blood loss in connection with cardiac surgery, including cardiopulmonary bypass operations.

However, when administered in vivo, aprotinin has been found to have a nephrotoxic effect in rats, rabbits and dogs after repeated injections of relatively high doses. The nephrotoxicity (appearing, i.e., in the form of lesions) observed for aprotinin might be ascribed to the accumulation of aprotinin in the proximal tubulus cells of the kidneys as a result of the high positive net charge of aprotinin, which causes it to be bound to the negatively charged surfaces of the tubuli. This nephrotoxicity makes aprotinin less suitable for clinical purposes, particularly in those uses requiring administration of large doses of the inhibitor (such as cardiopulmonary bypass operations). Furthermore, aprotinin is a bovine protein, which may induce an immune response upon administration to humans.

Thus there is a need for serine proteinase inhibitors which are not toxic for the treatment of acute pancreatitis, various states of shock syndrome, hyperfibrinolytic hemorrhage and myocardial infarction.

SUMMARY OF THE INVENTION

The present invention fills this need by providing for a new class of proteinase inhibitors called disulfide core proteinase inhibitors (hereinafter referred to as a Zdsc1 polypeptide). Murine Zdsc1, SEQ ID NOs: 1 and 2 has a signal sequence extending from the methionine at position 1 through and including the alanine at position 24 of SEQ ID NO:2. The mature murine Zdsc1 polypeptide is also depicted by SEQ ID NO:3. SEQ ID NO:4 and 5 are examples of a mature human Zdsc1 polypeptide and polynucleotide which encodes it. A generic Zdsc1 polypeptide is exemplified by SEQ ID NO:6.

Within one aspect of the invention there is provided an isolated polypeptide. The polypeptide being comprised of a sequence of amino acids containing the sequence of SEQ ID NO:2, SEQ ID NO:3 or SEQ ID NO:5.

Within another aspect of the invention there is provided an isolated polynucleotide which encodes a polypeptide comprised of a sequence of amino acids containing the sequence of SEQ ID NO:2, SEQ ID NO:3 or SEQ ID NO:5.

Within an additional aspect of the invention there is provided a polynucleotide sequence which hybridizes under stringent conditions to either SEQ ID NO:1 or SEQ ID NO:4 or to a complementary sequence of SEQ ID NO:1 or to a complementary sequence of SEQ ID NO:4.

Within an additional aspect of the invention there is provided a polynucleotide sequence which is at least 90%, 95%, or 99% homologous to a polynucleotide sequence which encodes the polypeptide of SEQ ID NO:3 or SEQ ID NO:4.

Within another aspect of the invention there is provided an expression vector comprising (a) a transcription promoter; (b) a DNA segment encoding a Zdsc1 polypeptide, containing an amino acid sequence as described above.

Within another aspect of the invention there is provided a cultured eukaryotic, bacterial, fungal or other cell into which has been introduced an expression vector as disclosed above, wherein said cell expresses a mammalian Zdsc1 polypeptide encoded by the DNA segment.

Within another aspect of the invention there is provided a chimeric polypeptide consisting essentially of a first portion and a second portion joined by a peptide bond. The first portion of the chimeric polypeptide consists essentially of a Zdsc1 polypeptide as described above. The invention also provides expression vectors encoding the chimeric polypeptides and host cells transfected to produce the chimeric polypeptides.

Within an additional aspect of the invention there is provided an antibody that specifically binds to a polypeptide as disclosed above and an anti-idiotypic antibody of an antibody which specifically binds to a Zdsc1 antibody.

These and other aspects of the invention will become evident upon reference to the following detailed description of the invention.

DETAILED DESCRIPTION OF THE INVENTION

All references cited herein are incorporated in their entirety herein by reference.

Prior to setting forth the invention in detail, it may be helpful to the understanding thereof to define the following terms.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A, Nilsson et al., *EMBO J.* 4:1075 (1985); Nilsson et al., *Methods Enzymol.* 198:3 (1991), glutathione S transferase, Smith and Johnson, *Gene* 67:31, 1988), Glu-Glu affinity tag, Grussenmeyer et al., *Proc. Natl. Acad. Sci. USA* 82:7952–4 (1985), substance P, Flag™ peptide (Hopp et al., *Biotechnology* 6:1204–10 (1988), streptavidin binding peptide, or other antigenic epitope or binding domain. See, in general, Ford et al, *Protein Expression and Purification* 2: 95–107 (1991). DNAs encoding affinity tags are available from commercial suppliers, (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78 (1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-domain (Frank Grant suggests "multi-peptide" in that subunit binding and signal transduction can be separate subunits) structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene.

Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

Serine proteinase inhibitors regulate the proteolytic activity of target proteinases by occupying the active site and thereby preventing occupation by normal substrates. Although serine proteinase inhibitors fall into several unrelated structural classes, they all possess an exposed loop (variously termed an "inhibitor loop", a "reactive core", a "reactive site", a "binding loop") which is stabilized by intermolecular interactions between residues flanking the binding loop and the protein core. See Bode, W. and Huber, R. "Natural protein proteinase inhibitors and their interactions with proteinases", *Eur. J. Biochem.*, 204: 433–451 (1992). Interaction between inhibitor and enzyme produces a stable complex which disassociates very slowly, producing either virgin or a modified inhibitor which is cleaved at the scissile bond of the binding loop.

Serine proteinase inhibitors fall into various structural families, for example, the Kunitz family, the Kazal family, and the Hirudin family. The protein Zdsc1 is a member of a new subfamily, which appears to be closely related to the Chelonianin family. The Chelonianin family is characterized by a common structural motif which comprises two adjacent beta-hairpin motifs, each consisting of two antiparallel beta strands connected by a loop region. The secondary structure of this motif is depicted by beta-sheet topology K (Branden, C. and Tooze, J. Introduction to Protein Structure. p. 28 (GarlandPublishing, Inc., 1991). The beta strands are linked by intra-chain hydrogen bonding and by a network of four disulfide bonds. These disulfide bonds stabilize the structure of the proteinase inhibitor and render it less susceptible to degradation. This structural feature has caused the Chelonianin family to be referred to as the "four-disulfide core" family of proteinase inhibitors. This family includes human antileukoproteinase, human elafin, guinea pig caltrin-like protein, human kallman syndrome protein, sea turtle chelonianin, and human epididymal secretory protein E4, and trout TOP-2, and C. Elegans C08G9. Several of these family members contain several copies of this structural motif.

Imbalances between native proteinases and a proteinase inhibitor is seen in patients where levels of human antileukoproteinase inhibitor are compromised by genetic background or by air contamination. In these patients, severe lung damage can result due to unmitigated activity of proteinases. The elastase inhibitory domain of antileukoproteinase inhibitor falls into the four-disulfide core family, which is related to the three-disulfide core family of zdsc1. As another example, human elafin (also in the four-disulfide core family) is a specific inhibitor of leukocyte elastase and pancreatic elastase. These proteinases have the ability to cleave the connective tissue protein elastin and therefore elafin may prevent excessive elastase-mediated tissue proteolysis and damage.

Serine proteinase inhibitor activity can be measured using the method essentially described by Norris et al., *Biol Chem. Hoppe-Seyler* 371: 37–42 (1990). Briefly, various fixed concentrations of the Kunitz-type inhibitor are incubated in the presence of serine proteinases at the concentrations listed in Table 1 in 100 mM NaCl, 50 mM Tris HCl, 0.01 TWEEN80 (Polyoxyethylenesorbitan monoleate) (pH 7.4) at 25° C. After a 30 minute incubation, the residual enzymatic activity is measured by the degradation of a solution of the appropriate substrate as listed in Table 1 in assay buffer. The samples are incubated for 30 minutes after which the absorbance of each sample is measured at 405 nm. An inhibition of enzyme activity is measured as a decrease in absorbance at 405 nm or fluorescence Em at 460 nm. From the results, the apparent inhibition constant $K_i$ is calculated.

TABLE 1

| Protease (concentration) Source | Substrate (concentration) Source |
|---|---|
| Trypsin (8 nM) Novo Nordisk A/S, Bagsvaerd, Denmark | H-D-Val-Leu-Lys-pNA (0.6 mM) Kabi |
| Chymotrypsin (2.5 nM) Novo Nordisk A/S | MeO-Suc-Arg-Pro-Tyr-pNA (0.6 mM) Kabi |
| GL Kallikrein (1 U/ml) Sigma, St Louis, MO | H-D-Val-Leu-Arg-pNA (0.6 mM) Kabi |
| Plasmin (10 nM) Kabi | H-D-Val-Leu-Lys-pNA (0.6 mM) Kabi |
| Urokinase (5 nM) Serono Freigurg, Germany | <Glu-Gly-Arg-pNA (0.6 mM) Kabi |
| rec. Protein Ca (5 nM) Novo Nordisk A/S | <Glu-Pro-Arg-pNA (0.6 mM) Kabi |
| PL Kallikrein (3 nM) Kabi | H-D-Pro-Phe-Arg-pNA (0.6 mM) Kabi |
| human Factor XIIa (30 nM) Dr. Walt Kisiel University of New Mexico, Albuquerque, NM | H-D-Pro-Phe-Arg-pNA (0.6 mM) Kabi |
| human Factor XIa (1 nM) Dr. Kazuo Fujikawa University of Washington, Seattle, WA | Boc-Glu(OBzl)-Ala-Arg-MCA (0.12 mM) Peptide Institute Osaka, Japan |
| human Factor Xa (3 nM) Dr. I. Schousboe Copenhagen, Denmark | MeO-CO-CHA-Gly-Arg-pNA (0.3 mM) NycoMed Oslo, Norway |
| rec. human Factor VIIa | H-D-Ile-Pro-Arg-pNA (0.6 mM) |

TABLE 1-continued

| Protease (concentration) Source | Substrate (concentration) Source |
|---|---|
| (300 nM) Novo Nordisk A/S Leukocyte Elastase purified at Novo Nordisk A/S using the method of Baugh and Travis (Biochemistry 15: 836–843, 1976) | Kabi MeO-Suc-Ala-Ala-Pro-Val-pNA (0.6 mM) (SEQ ID NO:14) Sigma Chemical Co. St. Louis, MO |
| Cathepsin G purified at Novo Nordisk A/S using the method of Baugh and Travis (Biochemistry 15: 836–843, 1976) | Suc-Ala-Ala-Pro-Phe-pNA (0.6 mM) (SEQ ID NO:15) Sigma Chemical Co. |

Abbreviations in Table 1: rec. refers to recombinant, GL kallikrein refers to glandular kallikrein, and PL kallikrein refers to plasma kallikrein.

Inhibition assays were performed in microtiter wells in a total volume of 300 µl in 10 mM NaCl, 50 mM Tris-HCl (pH 7.4), 0.01% TWEEN80 (Polyoxyethylenesorbitan monoleate). Each reaction contained 1 µM of the sample inhibitor and one of the proteases at the concentration listed in Table 1. The reactions were incubated at 25° C. for ten minutes after which the appropriate chromogenic substrate was added to the final concentration listed in Table 1 and the final reaction was incubated for thirty minutes at 25° C. Amidolytic activity was measured at 405 nm or by fluorescence Em at 460 nm. Percent inhibition was determined relative to reactions carried out in the absence of inhibitor representing 100% activity or 0% inhibition.

The serine proteinase inhibitors of the present invention may be used in the disclosed methods for the treatment of, inter alia, acute pancreatitis, various states of shock syndrome, hyperfibrinolytic hemorrhage and myocardial infarction. The amyloid protein precursor homologues of the present invention may be used, inter alia, to generate antibodies for use in demonstrating tissue distribution of the precursor or for use in purifying such proteins.

Cysteines 3–8 in members of the four disulfide core family occur according to the motif:

Cys Xaa Xaa Xaa Xaa Xaa Cys Xaa Xaa Xaa Xaa Xaa Cys Cys Xaa Xaa Xaa Cys Xaa Cys Xaa Xaa Xaa Cys (SEQ ID NO:17) The residue Xaa can by any amino acid residue except for cysteine.

The spacing between cysteines 1–2 and between cysteines 2–3 in this family is variable. Cysteines 1–3 have been observed to occur according to one of the following motifs:

Cys Xaa Xaa Xaa Xaa Xaa Xaa Xaa Xaa Xaa Xaa Cys Xaa Xaa Xaa Cys (SEQ ID NO:18)

Cys Xaa Xaa Xaa Xaa Xaa Xaa Cys Xaa Xaa Xaa Xaa Xaa Xaa Xaa Cys (SEQ ID NO:19)

Cys Xaa Xaa Xaa Xaa Xaa Xaa Xaa Xaa Xaa Xaa Cys Xaa Xaa Xaa Cys (SEQ ID NO:20)

Cys Xaa Xaa Xaa Xaa Xaa Xaa Xaa Cys Xaa Xaa Cys (SEQ ID NO:21)

Cys Xaa Xaa Xaa Xaa Xaa Xaa Xaa Xaa Xaa Cys Xaa Xaa Xaa Cys (SEQ ID NO:22)

The 8 cysteines in the four-disulfide core are bonded according to the pattern: 1–6, 2–7, 3–5, 4–8

Zdsc1

The protein Zdsc1 is a member of a new related subfamily, which will be referred to as the "three-disulfide core" family. This family is distinct from the four-disulfide core family due to the absence of cysteines 1 and 6. The remaining 6 cysteines occur according to the pattern:

Cys Xaa Xaa Xaa Cys Xaa Xaa Xaa Xaa Xaa Cys Xaa Xaa Xaa Xaa Xaa Cys Xaa Xaa Xaa Xaa Cys Xaa Xaa Xaa Cys (SEQ ID NO:23).

Zdsc1 is related by sequence homology to most of the four-disulfide core proteins, having the highest similarity to trout TOP-2 and mouse WDMN1 protein. See Garczynski, M. and Goetz, F. Molecular characterization of a RNA transcript that is highly up-regulated at the time of ovulation in the brook trout ovary, *Biology of Reproduction*, 57: 856–864 (1997).

To further characterize the three-dimensional structure of Zdsc1, including the disulfide bonding pattern and binding loop, we have constructed a homology model based on the NMR structure for porcine elafin, FLE, Francart, C. et al "Solution structure of R-elafin, a specific inhibitor of elastase", *J. Mol. Biol.* 268: 666–677 (1997). The multiple alignment between the three proteins is given below. By analogy with the known and predicted structure/function relationships in elafin and the crystal structure of antileukoproteinase complexed with chymotrypsin certain features of Zdsc1/2 can be predicted. See Grutter, M. et al., "The 2.5A X-ray crystal structure of the acid-stable proteinase inhibitor from human mucous secretions analyzed in its complex with bovine alpha-chymotrypsin", *EMBO J.*, 7: 345–351 (1988). The 6 cysteines in Zdsc1 are bonded according to the pattern:

2–7, 3–5, 4–8

The reactive binding loop of Zdsc1 includes the sequence LQLLGT (SEQ ID NO: 9). Their active binding loop of human Zdsc includes the sequence DRLLGT (SEQ ID NO: 10). In Zdsc1 flanking residues around this binding loop are expected to interact with the target proteinase. The scissile bond is in the reactive binding loop between the two Leucines. Substitution at the P1 position (the second Leucine) is not tolerated as this residue is predicted to influence specificity towards the target proteinase, Bode, W. and Huber, R. "Natural protein proteinase inhibitors and their interactions with proteinases", *Eur. J. Biochem.*, 204: 433–451 (1992). Substitution of any cysteine residue is not tolerated as this is predicted to significantly destabilize the structure.

To predict the variation acceptable from positions Gln30 through Cys60 in Zdsc1 we have created a generalized motif which enumerates the permissible substitutions at each position.

```
            MKLGAFLLLVSLITLSLEVQELQA (SEQ ID NO:8)
            (The predicted signal sequence for Zdsc1)

3    4    56  7   8
FLE:      IILIRCAMLNPPNRCLKDTDCPGIKKCCEGSCGMACFVPQ  (SEQ ID NO:7)

ZDSC1 (m):AVRPLQLLGTCAELCRGDWDCGPEEQCVSIGCSHICTTN   (SEQ ID NO:3)

ZDSC1 (h): AGDRLLGTCVELCTGDWDCNPGDHCVSNGCGHECVAG    (SEQ ID NO:5)

2    3    4   5   7   8
```

Multiple alignment between porcine elafin, and the predicted mature peptide for Zdsc1. Cysteines 3–8 of FLE are labeled on the top of the alignment. Cysteines 1–6 of Zdsc1 are labeled on the bottom of the alignment, using the standard numbering for four-disulfide core proteins. Based upon the analysis of Zdsc1 and Zdsc2 the following generic protein has been deduced as shown below in SEQ ID NO: 6.

```
                        SEQ ID NO:6
       Xaa Xaa Xaa Xaa Xaa Xaa Leu Leu Gly Thr Cys Xaa Glu Leu
                                Cys Xaa 5                    10                  15
       Gly Asp Trp Asp Cys Xaa Pro Xaa Xaa Xaa Cys Val Ser Xaa
                              Gly Cys 20                   25             30
                Xaa His Xaa Cys Xaa Xaa Xaa
                                35
``` where in

Xaa at amino acid position 1 is Ala or is absent;

Xaa at amino acid position 2 is Val or is absent;

Xaa at amino acid position 3 is Arg or Ala;

Xaa at amino acid position 4 is Pro or Gly;

Xaa at amino acid position 5 is Leu or Asp;

Xaa at amino acid position 6 is Gln, Arg, Lys or Glu;

Xaa at amino acid position 12 is Val, Ala, Ile, Leu, Met or Ser;

Xaa at amino acid position 16 is Thr, Arg, Ala, Asn, Ser, Val, Gln, Glu, His or Lys;

Xaa at amino acid position 22 is Asn, Gly, Asp, His or Ser;

Xaa at amino acid position 24 is Ala, Arg, Asn, Asp, Glu, Gln, Gly, His, Lys, Pro, Ser, or Thr;

Xaa at amino acid position 25 is Asp or Glu

Xaa at amino acid position 26 is His, Gln Tyr or Glu;

Xaa at amino acid position 30 is Ala, Arg, Asn, Asp, Gln, Glu, Gly His, Ile, Leu, Lys, Met, Phe, Ser, Thr, Tyr, or Val;

Xaa at amino acid position 33 is Gly, Ser, Ala, Asn, Thr;

Xaa at amino acid position 35 is Ala, Arg, Asn, Asp, Glu, Gln, Gly, His, Ile, Leu, Lys, Met Phe, Pro, Ser, Thr, Trp, Tyr or Val;

Xaa at amino acid position 37 is Val or Thr;

Xaa at amino acid position 38 is Ala or Thr; and

Xaa at amino acid position 39 is Asn or Gly.

Any resultant polypeptide based upon SEQ ID NO: 8 must be at least 80%, preferably 90 or 95% and most preferably 99% identical to SEQ ID NO: 3, SEQ ID NO: 5 or to SEQ ID NO:7.

POLYNUCLEOTIDES:

The present invention also provides polynucleotide molecules, including DNA and RNA molecules, that encode the Zdsc polypeptides disclosed herein. Those skilled in the art will readily recognize that, in view of the degeneracy of the genetic code, considerable sequence variation is possible among these polynucleotide molecules. Polynucleotides, generally a cDNA sequence, of the present invention encode the described polypeptides herein. A cDNA sequence which encodes a polypeptide of the present invention is comprised of a series of codons, each amino acid residue of the polypeptide being encoded by a codon and each codon being comprised of three nucleotides. The amino acid residues are encoded by their respective codons as follows.

Alanine (Ala) is encoded by GCA, GCC, GCG or GCT;

Cysteine (Cys) is encoded by TGC or TGT;

Aspartic acid (Asp) is encoded by GAC or GAT;

Glutamic acid (Glu) is encoded by GAA or GAG;

Phenylalanine (Phe) is encoded by TTC or TTT;

Glycine (Gly) is encoded by GGA, GGC, GGG or GGT;

Histidine (His) is encoded by CAC or CAT;

Isoleucine (Ile) is encoded by ATA, ATC or ATT;

Lysine (Lys) is encoded by AAA, or AAG;

Leucine (Leu) is encoded by TTA, TTG, CTA, CTC, CTG or CTT;

Methionine (Met) is encoded by ATG;

Asparagine (Asn) is encoded by AAC or AAT;

Proline (Pro) is encoded by CCA, CCC, CCG or CCT;

Glutamine (Gln) is encoded by CAA or CAG;

Arginine (Arg) is encoded by AGA, AGG, CGA, CGC, CGG or CGT;

Serine (Ser) is encoded by AGC, AGT, TCA, TCC, TCG or TCT;

Threonine (Thr) is encoded by ACA, ACC, ACG or ACT;

Valine (Val) is encoded by GTA, GTC, GTG or GTT;

Tryptophan (Trp) is encoded by TGG; and

Tyrosine (Tyr) is encoded by TAC or TAT.

It is to be recognized that according to the present invention, when a polynucleotide is claimed as described herein, it is understood that what is claimed are both the sense strand, the anti-sense strand, and the DNA as double-stranded having both the sense and anti-sense strand annealed together by their respective hydrogen bonds. Also claimed is the messenger RNA (mRNA) which encodes the polypeptides of the president invention, and which mRNA is encoded by the cDNA described herein. Messenger RNA (mRNA) will encode a polypeptide using the same codons as those defined herein, with the exception that each thymine nucleotide (T) is replaced by a uracil nucleotide (U).

One of ordinary skill in the art will also appreciate that different species can exhibit "preferential codon usage." In general, see, Grantham, et al., *Nuc. Acids Res.* 8:1893–912 (1980); Haas, et al. *Curr. Biol.* 6:315–24 (1996); Wain-Hobson, et al., *Gene* 13:355–64 (1981); Grosjean and Fiers, *Gene* 18:199–209 (1982); Holm, *Nuc. Acids Res.* 14:3075–87 (1986); Ikemura, *J. Mol. Biol.* 158:573–97 (1982). As used herein, the term "preferential codon usage" or "preferential codons" is a term of art referring to protein translation codons that are most frequently used in cells of a certain species, thus favoring one or a few representatives of the possible codons encoding each amino acid. For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Sequences containing preferential codons can be tested and optimized for expression in various species, and tested for functionality as disclosed herein.

Within preferred embodiments of the invention the isolated polynucleotides will hybridize to similar sized regions of SEQ ID NO:1, SEQ ID NO:4, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is up to about 0.03 M at pH 7 and the temperature is at least about 60° C.

As previously noted, the isolated polynucleotides of the present invention include DNA and RNA. Methods for preparing DNA and RNA are well known in the art. In general, RNA is isolated from a tissue or cell that produces large amounts of Zdsc1 RNA. Such tissues and cells are identified by Northern blotting, Thomas, *Proc. Natl. Acad. Sci. USA* 77:5201 (1980), and include high expression of human Zdsc1 in the liver. Total RNA can be prepared using guanidine HCl extraction followed by isolation by centrifugation in a CsCl gradient, Chirgwin et al., *Biochemistry* 18:52–94, 1979). Poly (A)$^+$ RNA is prepared from total RNA using the method of Aviv and Leder, *Proc. Natl. Acad. Sci. USA* 69:1408–1412 (1972). Complementary DNA (cDNA) is prepared from poly(A)$^+$ RNA using known methods. In the alternative, genomic DNA can be isolated. Polynucleotides encoding Zdsc polypeptides are then identified and isolated by, for example, hybridization or PCR.

A full-length clone encoding Zdsc1 polypeptide can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to Zdsc, receptor fragments, or other specific binding partners.

The polynucleotides of the present invention can also be synthesized using gene machines. Currently the method of choice is the phosphoramidite method. If chemically synthesized double stranded DNA is required for an application such as the synthesis of a gene or a gene fragment, then each complementary strand is made separately. The production of short genes (60 to 80 bp) is technically straightforward and can be accomplished by synthesizing the complementary strands and then annealing them. For the production of longer genes (>300 bp), however, special strategies must be invoked, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. The double-stranded constructs are sequentially linked to one another to form the entire gene sequence. Because it is absolutely essential that a chemically synthesized gene have the correct sequence of nucleotides, each double-stranded fragment and then the complete sequence is characterized by DNA sequence analysis. See Glick and Pasternak, *Molecular Biotechnology, Principles & Applications of Recombinant DNA*, (ASM Press, Washington, D.C. 1994); Itakura et al., *Annu. Rev. Biochem.* 53: 323–56 (1984) and Climie et al., *Proc. Natl. Acad. Sci. USA* 87:633–637 (1990).

The present invention further provides counterpart polypeptides and polynucleotides from other species (orthologs). These species include, but are not limited to mammalian, avian, amphibian, reptile, fish, insect and other vertebrate and invertebrate species. Of particular interest are Zdsc polypeptides from other mammalian species, including murine, porcine, ovine, bovine, canine, feline, equine, and other primate polypeptides. Orthologs of human Zdsc can be cloned using information and compositions provided by the present invention in combination with conventional cloning techniques. For example, a cDNA can be cloned using mRNA obtained from a tissue or cell type that expresses Zdsc as disclosed herein. Suitable sources of mRNA can be identified by probing Northern blots with probes designed from the sequences disclosed herein. A library is then prepared from mRNA of a positive tissue or cell line. A Zdsc-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human Zdsc sequence disclosed herein. Within an additional method, the cDNA library can be used to transform or transfect host cells, and expression of the cDNA of interest can be detected with an antibody to Zdsc1 polypeptide. Similar techniques can also be applied to the isolation of genomic clones.

Those skilled in the art will recognize that the sequences disclosed in SEQ ID NO:1 and SEQ ID NO:4 represent a single alleles of murine Zdsc1 and human Zdsc1 respectively, and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the Zdsc1 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

optimize the alignment scores using a gap opening penalty of 10, a gap extension penalty of 1, and the "blosum 62" scoring matrix of Henikoff and Henikoff (ibid.) as shown in Table 2 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 2

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

The present invention also provides isolated Zdsc1 polypeptides that are substantially identical to the polypeptides of SEQ ID NO:2, SEQ ID NO:3 and SEQ ID NO:5 and their orthologs. The term "substantially identical" is used herein to denote polypeptides having 50%, preferably 60%, more preferably at least 80%, sequence identity to the sequences shown in SEQ ID NO:2 or their orthologs. Such polypeptides will more preferably be at least 90% identical, and most preferably 95% or more identical to SEQ ID NO:2 or its orthologs.) Percent sequence identity is determined by conventional methods. See, for example, Altschul et al., *Bull. Math. Bio.* 48: 603–616 (1986) and Henikoff and Henikoff, *Proc. Natl. Acad. Sci. USA* 89:10915–10929 (1992). Briefly, two amino acid sequences are aligned to Those skilled in the art appreciate that there are many established algorithms to align two amino acid sequences. The "FASTA" similarity search algorithm of Pearson and Lipman is a suitable protein alignment method for examining the level of identity shared by an amino acid sequence and the amino acid sequence of a putative variant. The FASTA algorithm is described by Pearson and Lipman, *Proc. Nat'l Acad. Sci. USA* 85:2444 (1988), and by Pearson, *Meth. Enzymol.* 183:63 (1990). Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from four to six.

The present invention includes nucleic acid molecules that encode a polypeptide having one or more conservative amino acid changes, compared with the amino acid sequence of SEQ ID NO:3 or with the amino acid sequence of SEQ ID NO:5. The BLOSUM62 table is an amino acid substitution matrix derived from about 2,000 local multiple alignments of protein sequence segments, representing highly conserved regions of more than 500 groups of related proteins [Henikoff and Henikoff, *Proc. Nat'l Acad. Sci. USA* 89:10915 (1992)]. Accordingly, the BLOSUM62 substitution frequencies can be used to define conservative amino acid substitutions that may be introduced into the amino acid sequences of the present invention. As used herein, the language "conservative amino acid substitution" refers to a substitution represented by a BLOSUM62 value of greater than −1. For example, an amino acid substitution is conservative if the substitution is characterized by a BLOSUM62 value of 0,1,2, or 3. Preferred conservative amino acid substitutions are characterized by a BLOSUM62 value of at least 1 (e.g., 1,2 or 3), while more preferred conservative substitutions are characterized by a BLOSUM62 value of at least 2 (e.g., 2 or 3). Accordingly the present invention claims those polypeptides which are at least 90%, preferably 95% and most preferably 99% identical to SEQ ID NO:3 and which are able to stimulate antibody production in a mammal, and said antibodies are able to bind the native sequence of SEQ ID NO:3.

Variant Zdsc1 polypeptides or substantially identical Zdsc1 polypeptides are characterized as having one or more amino acid substitutions, deletions or additions. These changes are preferably of a minor nature, that is conservative amino acid substitutions (see Table 3) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20–25 residues, or an affinity tag. Polypeptides comprising affinity tags can further comprise a proteolytic cleavage site between the Zdsc polypeptide and the affinity tag. Preferred such sites include thrombin cleavage sites and factor Xa cleavage sites.

TABLE 3

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

Different species can exhibit "preferential codon usage." In general, see, Grantham et al., *Nuc. Acids Res.* 8:1893 (1980), Haas et al. *Curr. Biol.* 6:315 (1996), Wain-Hobson et al., *Gene* 13:355 (1981), Grosjean and Fiers, *Gene* 18:199 (1982), Holm, *Nuc. Acids Res.* 14:3075 (1986), Ikemura, *J. Mol. Biol.* 158:573 (1982), Sharp and Matassi, *Curr. Opin. Genet. Dev.* 4:851 (1994), Kane, *Curr. Opin. Biotechnol.* 6:494 (1995), and Makrides, *Microbiol. Rev.* 60:512 (1996). As used herein, the term "preferential codon usage" or "preferential codons" is a term of art referring to protein translation codons that are most frequently used in cells of a certain species, thus favoring one or a few representatives of the possible codons encoding each amino acid. For example, the amino acid Threonine (Thr) may be encoded by ACA, ACC, ACG, or ACT, but in mammalian cells, ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Sequences containing preferential codons can be tested and optimized for expression in various species, and tested for functionality as disclosed herein.

The present invention further provides variant polypeptides and nucleic acid molecules that represent counterparts from other species (orthologs). These species include, but are not limited to mammalian, avian, amphibian, reptile, fish, insect and other vertebrate and invertebrate species. Of particular interest are Zdsc1 polypeptides from other mammalian species, including murine, porcine, ovine, bovine, canine, feline, equine, and other primate polypeptides. Orthologs of human Zdsc1 can be cloned using information and compositions provided by the present invention in combination with conventional cloning techniques. For example, a cDNA can be cloned using mRNA obtained from a tissue or cell type that expresses Zdsc1 as disclosed herein. Suitable sources of mRNA can be identified by probing northern blots with probes designed from the sequences disclosed herein. A library is then prepared from mRNA of a positive tissue or cell line.

An Zdsc1-encoding cDNA can then be isolated by a variety of methods, such as by probing with a complete or partial human cDNA or with one or more sets of degenerate probes based on the disclosed sequences. A cDNA can also be cloned using the polymerase chain reaction with primers designed from the representative human Zdsc1 sequences disclosed herein. Within an additional method, the cDNA library can be used to transform or transfect host cells, and expression of the cDNA of interest can be detected with an antibody to Zdsc1 polypeptide. Similar techniques can also be applied to the isolation of genomic clones.

Those skilled in the art will recognize that the sequence disclosed in SEQ ID NO:1 represents a single allele of human Zdsc1, and that allelic variation and alternative splicing are expected to occur. Allelic variants of this sequence can be cloned by probing cDNA or genomic libraries from different individuals according to standard procedures. Allelic variants of the nucleotide sequences shown in SEQ ID NO:1 or SEQ ID NO:4, including those containing silent mutations and those in which mutations result in amino acid sequence changes, are within the scope of the present invention, as are proteins which are allelic variants of SEQ ID NO:2, SEQ ID NO:3 or SEQ ID NO:5. cDNA molecules generated from alternatively spliced mRNAs, which retain the properties of the Zdsc1 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

A pair of nucleic acid molecules, such as DNA-DNA, RNA-RNA and DNA-RNA, can hybridize if the nucleotide sequences have some degree of complementarity. Hybrids can tolerate mismatched base pairs in the double helix, but the stability of the hybrid is influenced by the degree of mismatch. The $T_m$ of the mismatched hybrid decreases by 1° C. for every 1–1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases. Stringent hybridization conditions encompass temperatures of about 5–25° C. below the $T_m$ of the hybrid and a hybridization buffer having up to 1 M $Na^+$. Higher degrees of stringency at lower temperatures can be achieved with the addition of formamide which reduces the $T_m$ of the hybrid about 1° C. for each 1% formamide in the buffer solution. Generally, such 5 stringent conditions include temperatures of 20–70° C. and a hybridization buffer containing up to 6×SSC and 0–50% formamide. A higher degree of stringency can be achieved at temperatures of from 40–70° C. with a hybridization buffer having up to 4×SSC and from 0–50% formamide. Highly stringent conditions typically encompass temperatures of 42–70° C. with a hybridization buffer having up to 1×SSC and 0–50% formamide. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes.

The above conditions are meant to serve as a guide and it is well within the abilities of one skilled in the art to adapt these conditions for use with a particular polypeptide hybrid. The $T_m$ for a specific target sequence is the temperature (under defined conditions) at which 50% of the target sequence will hybridize to a perfectly matched probe sequence. Those conditions which influence the $T_m$ include, the size and base pair content of the polynucleotide probe, the ionic strength of the hybridization solution, and the presence of destabilizing agents in the hybridization solution. Numerous equations for calculating $T_m$ are known in the art, and are specific for DNA, RNA and DNA-RNA hybrids and polynucleotide probe sequences of varying length (see, for example, Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and Primer Premier 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences, >50 base pairs, is performed at temperatures of about 20–25° C. below the calculated $T_m$. For smaller probes, <50 base pairs, hybridization is typically carried out at the $T_m$ or 5–10° C. below. This allows for the maximum rate of hybridization for DNA-DNA and DNA-RNA hybrids.

The length of the polynucleotide sequence influences the rate and stability of hybrid formation. Smaller probe sequences, <50 base pairs, reach equilibrium with complementary sequences rapidly, but may form less stable hybrids. Incubation times of anywhere from minutes to hours can be used to achieve hybrid formation. Longer probe sequences come to equilibrium more slowly, but form more stable complexes even at lower temperatures. Incubations are allowed to proceed overnight or longer. Generally, incubations are carried out for a period equal to three times the calculated Cot time. Cot time, the time it takes for the polynucleotide sequences to reassociate, can be calculated for a particular sequence by methods known in the art.

The base pair composition of polynucleotide sequence will effect the thermal stability of the hybrid complex, thereby influencing the choice of hybridization temperature and the ionic strength of the hybridization buffer. A-T pairs are less stable than G-C pairs in aqueous solutions containing sodium chloride. Therefore, the higher the G-C content, the more stable the hybrid. Even distribution of G and C residues within the sequence also contribute positively to hybrid stability. In addition, the base pair composition can be manipulated to alter the $T_m$ of a given sequence. For example, 5-methyldeoxycytidine can be substituted for deoxycytidine and 5-bromodeoxuridine can be substituted for thymidine to increase the $T_m$, whereas 7-deazz-2'-deoxyguanosine can be substituted for guanosine to reduce dependence on $T_m$.

The ionic concentration of the hybridization buffer also affects the stability of the hybrid. Hybridization buffers generally contain blocking agents such as Denhardt's solution (Sigma Chemical Co., St. Louis, Mo.), denatured salmon sperm DNA, tRNA, milk powders (BLOTTO), heparin or SDS, and a $Na^+$ source, such as SSC (1×SSC: 0.15 M sodium chloride, 15 mM sodium citrate) or SSPE (1×SSPE: 1.8 M NaCl, 10 mM $NaH_2PO_4$, 1 mM EDTA, pH 7.7). By decreasing the ionic concentration of the buffer, the stability of the hybrid is increased. Typically, hybridization buffers contain from between 10 mM–1 M Na$^+$. The addition of destabilizing or denaturing agents such as formamide, tetralkylammonium salts, guanidinium cations or thiocyanate cations to the hybridization solution will alter the $T_m$ of a hybrid. Typically, formamide is used at a concentration of up to 50% to allow incubations to be carried out at more convenient and lower temperatures. Formamide also acts to reduce non-specific background when using RNA probes.

As an illustration, a nucleic acid molecule encoding a variant Zdsc1 polypeptide can be hybridized with a nucleic acid molecule having the nucleotide sequence of SEQ ID NO:1 (or its complement) at 42° C. overnight in a solution comprising 50% formamide, 5×SSC (1×SSC: 0.15 M sodium chloride and 15 mM sodium citrate), 50 mM sodium phosphate (pH 7.6), 5×Denhardt's solution (100×Denhardt's solution: 2% (w/v) Ficoll 400, 2% (w/v) polyvinylpyrrolidone, and 2% (w/v) bovine serum albumin), 10% dextran sulfate, and 20 µg/ml denatured, sheared salmon sperm DNA. One of skill in the art can devise variations of these hybridization conditions. For example, the hybridization mixture can be incubated at a higher temperature, such as about 65° C., in a solution that does not contain formamide. Moreover, premixed hybridization solutions are available (e.g., EXPRESSHYB Hybridization Solution from CLONTECH Laboratories, Inc.), and hybridization can be performed according to the manufacturer's instructions.

Following hybridization, the nucleic acid molecules can be washed to remove non-hybridized nucleic acid molecules under stringent conditions, or under highly stringent conditions. Typical stringent washing conditions include washing in a solution of 0.5×–2×SSC with 0.1% sodium dodecyl sulfate (SDS) at 55–65° C. That is, nucleic acid molecules encoding a variant Zdsc1 polypeptide hybridize with a nucleic acid molecule having the nucleotide sequence of SEQ ID NO:1 (or its complement) under stringent washing conditions, in which the wash stringency is equivalent to 0.5×–2×SSC with 0.1% SDS at 55–65° C., including 0.5× SSC with 0.1% SDS at 55° C., or 2×SSC with 0.1% SDS at 65° C. One of skill in the art can readily devise equivalent conditions, for example, by substituting SSPE for SSC in the wash solution.

Typical highly stringent washing conditions include washing in a solution of 0.1×–0.2×SSC with 0.1% sodium dodecyl sulfate (SDS) at 50–65° C. In other words, nucleic acid molecules encoding a variant Zdsc1 polypeptide hybridize with a nucleic acid molecule having the nucleotide sequence of SEQ ID NO:1 (or its complement) under highly stringent washing conditions, in which the wash stringency is equivalent to 0.1×–0.2×SSC with 0.1% SDS at 50–65° C., including 0.1×SSC with 0.1% SDS at 50° C., or 0.2×SSC with 0.1% SDS at 65° C.

The present invention also provides isolated Zdsc1 polypeptides that have a substantially similar sequence identity to the polypeptides of SEQ ID NO:2, or their orthologs. The term "substantially similar sequence identity" is used herein to denote polypeptides having at least 70%, at least 80%, at least 90%, at least 95% or greater than 95% sequence identity to the sequences shown in SEQ ID NO:2, or their orthologs. The present invention also includes polypeptides that comprise an amino acid sequence having at least 70%, at least 80%, at least 90%, at least 95% or greater than 95% sequence identity to the sequence of amino acid residues of SEQ ID NO:3. The present invention further includes nucleic acid molecules that encode such polypeptides. Methods for determining percent identity are described below.

The present invention also contemplates Zdsc1 variant nucleic acid molecules that can be identified using two criteria: a determination of the similarity between the encoded polypeptide with the amino acid sequence of SEQ ID NO:3, and a hybridization assay, as described above. Such Zdsc1 variants include nucleic acid molecules (1) that hybridize with a nucleic acid molecule having the nucleotide sequence of SEQ ID NO:1 (or its complement) under stringent washing conditions, in which the wash stringency is equivalent to 0.5×–2×SSC with 0.1% SDS at 55–65° C., and (2) that encode a polypeptide having at least 70%, at least 80%, at least 90%, at least 95% or greater than 95% sequence identity to the amino acid sequence of SEQ ID NO:3. Alternatively, Zdsc1 variants can be characterized as nucleic acid molecules (1) that hybridize with a nucleic acid molecule having the nucleotide sequence of SEQ ID NO:1 (or its complement) under highly stringent washing conditions, in which the wash stringency is equivalent to 0.1×–0.2×SSC with 0.1% SDS at 50–65° C., and (2) that encode a polypeptide having at least 70%, at least 80%, at least 90%, at least 95% or greater than 95% sequence identity to the amino acid sequence of SEQ ID NO:2.

The present invention further provides a variety of other polypeptide fusions [and related multimeric proteins comprising one or more polypeptide fusions]. For example, a Zdsc polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin-Zdsc1 polypeptide fusions can be expressed in genetically engineered cells [to produce a variety of multimeric Zdsc1 analogs]. Auxiliary domains can be fused to Zdsc1 polypeptides to target them to specific cells, tissues, or macromolecules (e.g., collagen). For example, a Zdsc1 polypeptide or protein could be targeted to a predetermined cell type by fusing a Zdsc1 polypeptide to a ligand that specifically binds to a receptor on the surface of the target cell. In this way, polypeptides and proteins can be targeted for therapeutic or diagnostic purposes. A Zdsc1 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1–9 (1996).

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs.

Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722 (1991); Ellman et al., *Methods Enzymol.* 202:301 (1991); Chung et al., *Science* 259:806–809 (1993); and Chung et al., *Proc. Natl. Acad. Sci. USA* 90:10145–10149 (1993). In a second method, translation is carried out in Xenopus oocytes by microinjection of mutated mRNA and chemically aminoacylated suppressor tRNAs, Turcatti et al., *J. Biol. Chem.* 271:19991–19998 (1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–7476 (1994). Naturally occurring amino acid residues can be converted to non-naturally occurring species by in vitro chemical modification. Chemical modification can be combined with site-directed mutagenesis to further expand the range of substitutions, Wynn and Richards, *Protein Sci.* 2:395–403 (1993).

A limited number of non-conservative amino acids, amino acids that are not encoded by the genetic code, non-naturally occurring amino acids, and unnatural amino acids may be substituted for Zdsc1 amino acid residues. Essential amino acids in the polypeptides of the present invention can be identified according to procedures known in the art, such as site-directed mutagenesis or alanine-scanning mutagenesis, Cunningham and Wells, *Science* 244: 1081–1085 (1989); Bass et al., *Proc. Natl. Acad. Sci. USA* 88:4498–4502 (1991). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699–4708 (1996). Sites of ligand-receptor or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–12 (1992); Smith et al., *J. Mol. Biol.* 224:899–904 (1992); Wlodaver et al., *FEBS Lett.* 309:59–64, 1992.

PROTEIN PRODUCTION:

The Zdsc1 polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual*, 2nd ed., (Cold Spring Harbor Laboratory Press, Cold Spring Harbor, N.Y., 1989), and Ausubel et al., eds., *Current Protocols in Molecular Biology*, (John Wiley and Sons, Inc., N.Y., 1987).

In general, a DNA sequence encoding a Zdsc1 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a Zdsc1 polypeptide into the secretory pathway of a host cell, a secretory signal sequence (also known as a leader sequence, prepro sequence or pre sequence) is provided in the expression vector. The secretory signal sequence may be that of Zdsc1, or may be derived from another secreted protein (e.g., t-PA) or synthesized de novo. The secretory signal sequence is operably linked to the Zdsc1 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein, such as a receptor. Such fusions may be used in vivo or in vitro to direct peptides through the secretory pathway.

Cultured mammalian cells are suitable hosts within the present invention. Methods for introducing exogenous DNA into mammalian host cells include calcium phosphate-mediated transfection, Wigler et al., *Cell* 14:725 (1978); Corsaro and Pearson, *Somatic Cell Genetics* 7:603 (1981): Graham and Van der Eb, *Virology* 52:456 (1973), electroporation, Neumann et al., *EMBO J.* 1:841–845 (1982), DEAE-dextran mediated transfection, Ausubel et al., ibid., and liposome-mediated transfection, Hawley-Nelson et al., *Focus* 15:73, 1993; Ciccarone et al., *Focus* 15:80 (1993), and viral vectors, Miller and Rosman, *BioTechniques* 7:980 (1989); Wang and Finer, *Nature Med.* 2:714 (1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72 (1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci.* (Bangalore) 11:47–58 (1987). Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from Autographa californica nuclear polyhedrosis virus (AcNPV). DNA encoding the Zdsc1 polypeptide is inserted into the baculoviral genome in place of the AcNPV polyhedrin gene coding sequence by one of two methods. The first is the traditional method of homologous DNA recombination between wild-type AcNPV and a transfer vector containing the Zdsc1 flanked by AcNPV sequences. Suitable insect cells, e.g. SF9 cells, are infected with wild-type AcNPV and transfected with a transfer vector comprising a Zdsc1 polynucleotide operably linked to an AcNPV polyhedrin gene promoter, terminator, and flanking sequences. See, King, L. A. and Possee, R. D., *The Baculovirus Expression System: A Laboratory Guide*, Chapman & Hall, (London); O'Reilly, D. R. et al., *Baculovirus Expression Vectors: A Laboratory Manual*, (Oxford University Press, New York, 1994); and, Richardson, C. D., Ed., *Baculovirus Expression Protocols. Methods in Molecular Biology*, (Humana Press, Totowa, N.J., 1995). Natural recombination within an insect cell will result in a recombinant baculovirus which contains Zdsc1 driven by the polyhedrin promoter. Recombinant viral stocks are made by methods commonly used in the art.

The second method of making recombinant baculovirus utilizes a transposon-based system described by Luckow, V. A, et al., *J Virol* 67:4566–79 (1993). This system is sold in the Bac-to-Bac kit (Life Technologies, Rockville, Md.). This system utilizes a transfer vector, pFastBac1™ (Life Technologies) containing a Tn7 transposon to move the DNA encoding the Zdsc1 polypeptide into a baculovirus genome maintained in *E. coli* as a large plasmid called a "bacmid." The pFastBac1™ transfer vector utilizes the AcNPV polyhedrin promoter to drive the expression of the gene of interest, in this case Zdsc1. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins, M. S. and Possee, R. D., *J Gen Virol* 71:971 (1990); Bonning, B. C. et al., *J Gen Virol* 75:1551 (1994); and, Chazenbalk, G. D., and Rapoport, B., *J Biol Chem* 270:1543 (1995). In such transfer vector constructs, a short or long version of the basic protein promoter can be used.

Moreover, transfer vectors can be constructed which replace the native Zdsc1 secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native Zdsc1 secretory signal sequence. In addition, transfer vectors can include an in-frame fusion with DNA encoding an epitope tag at the C- or N-terminus of the expressed Zdsc1 polypeptide, for example, a Glu-Glu epitope tag (Grussenmeyer, T. et al., *Proc Natl Acad Sci.* 82:7952–4, 1985). Using a technique known in the art, a transfer vector containing Zdsc1 is transformed into *E. coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses Zdsc1 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA* (ASM Press, Washington, D.C., 1994). Another suitable cell line is the High FiveO™ cell line (Invitrogen) derived from Trichoplusia ni (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the T. ni cells. The cells are grown up from an inoculation density of approximately $2-5\times10^5$ cells to a density of $1-2\times10^6$ cells at which time a recombinant viral stock is added at a multiplicity of infection (MOI) of 0.1 to 10, more typically near 3. The recombinant virus-infected cells typically produce the recombinant Zdsc1 polypeptide at 12–72 hours post-infection and secrete it with varying efficiency into the medium. The culture is usually harvested 48 hours post-infection. Centrifugation is used to separate the cells from the medium (supernatant). The supernatant containing the Zdsc1 polypeptide is filtered through micropore filters, usually 0.45 $\mu$m pore size. Procedures used are generally described in available laboratory manuals (King, L. A. and Possee, R. D., ibid.; O'Reilly, D. R. et al., ibid.; Richardson, C. D., ibid.). Subsequent purification of the Zdsc1 polypeptide from the supernatant can be achieved using methods described herein.

Fungal cells, including yeast cells, can also be used within the present invention. Yeast species of particular interest in this regard include *Saccharomyces cerevisiae, Pichia pastoris*, and *Pichia methanolica*. Methods for transforming S. cerevisiae cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in Saccharomyces cerevisiae is the POT1 vector system disclosed by Kawasaki et al. (U.S. Pat. No. 4,931,373), which allows transformed cells to be selected by growth in glucose-containing media.

Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including Hansenula polymorpha, Schizosaccharomyces pombe, Kluyveromyces lactis, Kluyveromyces fragilis, Ustilago maydis, Pichia pastoris, Pichia methanolica, Pichia guillermondii and Candida maltosa are known in the art. See, for example, Gleeson et al., J. Gen. Microbiol. 132:3459 (1986) and Cregg, U.S. Pat. No. 4,882,279. Aspergillus cells may be utilized according to the methods of McKnight et al., U.S. Pat. No. 4,935,349. Methods for transforming Acremonium chrysogenum are disclosed by Sumino et al., U.S. Pat. No. 5,162,228. Methods for transforming Neurospora are disclosed by Lambowitz, U.S. Pat. No. 4,486,533.

The use of Pichia methanolica as host for the production of recombinant proteins is disclosed in WIPO Publications WO 97/17450, WO 97/17451, WO 98/02536, and WO 98/02565. DNA molecules for use in transforming P. methanolica will commonly be prepared as double-stranded, circular plasmids, which are preferably linearized prior to transformation. For polypeptide production in P. methanolica, it is preferred that the promoter and terminator in the plasmid be that of a P. methanolica gene, such as a P. methanolica alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences.

A preferred selectable marker for use in Pichia memethanolica is a P. methanolica ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar proteinase genes (PEP4 and PRB1) are preferred. Electroporation is used to facilitate the introduction of a plasmid containing DNA encoding a polypeptide of interest into P. methanolica cells. It is preferred to transform P. methanolica cells by electroporation using an exponentially decaying, pulsed electric field having a field strength of from 2.5 to 4.5 kV/cm, preferably about 3.75 kV/cm, and a time constant ($\tau$) of from 1 to 40 milliseconds, most preferably about 20 milliseconds.

Prokaryotic host cells, including strains of the bacteria Escherichia coli, Bacillus and other genera are also useful host cells within the present invention. Techniques for transforming these hosts and expressing foreign DNA sequences cloned therein are well known in the art (see, e.g., Sambrook et al., ibid.). When expressing a Zdsc1 polypeptide in bacteria such as E. coli, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. P. methanolica cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for P. methanolica is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Protein Isolation

It is preferred to purify the polypeptides of the present invention to $\geq$80% purity, more preferably to $\geq$90% purity, even more preferably $\geq$95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant Zdsc1 polypeptides (or chimeric Zdsc1 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, (Pharmacia LKB Biotechnology, Uppsala, Sweden, 1988).

The polypeptides of the present invention can be isolated by exploitation of their properties. For example, immobilized metal ion adsorption (IMAC) chromatography can be used to purify histidine-rich proteins, including those comprising polyhistidine tags. Briefly, a gel is first charged with divalent metal ions to form a chelate, Sulkowski, *Trends in Biochem.* 3:1–7 (1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography, *Methods in Enzymol.*, Vol. 182, "Guide to Protein Purification", M. Deutscher, (ed.),pp. 529–539 (Acad. Press, San Diego, 1990). Within additional embodiments of the invention, a fusion of the polypeptide of interest and an affinity tag (e.g., maltose-binding protein, an immunoglobulin domain) may be constructed to facilitate purification. To direct the export of a receptor polypeptide from the host cell, the receptor DNA is linked to a second DNA segment encoding a secretory peptide, such as a t-PA secretory peptide.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. For example, part or all of a domain(s) conferring a biological function may be swapped between Zdsc1 of the present invention with the functionally equivalent domain(s) from another family member. Such domains include, but are not limited to, the secretory signal sequence, conserved motifs [provide list if possible], and [significant domains or regions in this family]. Such fusion proteins would be expected to have a biological functional profile that is the same or similar to polypeptides of the present invention depending on the fusion constructed. Moreover, such fusion proteins may exhibit other properties as disclosed herein. Zdsc1 polypeptides or fragments thereof may also be prepared through chemical synthesis. Zdsc1 polypeptides may be monomers or multimers; glycosylated or non-glycosylated; pegylated or non-pegylated; and may or may not include an initial methionine amino acid residue.

Antagonists are also useful as research reagents for characterizing sites of ligand-receptor interaction. Inhibitors of Zdsc1 activity (Zdsc1 antagonists) include anti-Zdsc1 antibodies and soluble Zdsc1 receptors, as well as other peptidic and non-peptidic agents (including ribozymes).

A Zdsc1 polypeptide can be expressed as a fusion with an immunoglobulin heavy chain constant region, typically an $F_c$ fragment, which contains two constant region domains and lacks the variable region. Methods for preparing such fusions are disclosed in U.S. Pat. Nos. 5,155,027 and 5,567,584. Such fusions are typically secreted as multimeric molecules wherein the Fc portions are disulfide bonded to each other and two non-Ig polypeptides are arrayed in closed proximity to each other. Fusions of this type can be used to affinity purify ligand, as an in vitro assay tool, antagonist). For use in assays, the chimeras are bound to a support via the $F_c$ region and used in an ELISA format.

Ligand-binding receptor polypeptides can also be used within other assay systems known in the art. Such systems include Scatchard analysis for determination of binding affinity, see Scatchard, *Ann. N.Y. Acad. Sci.* 51: 660 (1949) and calorimetric assays (Cunningham et al., *Science* 253:545 (1991); Cunningham et al., *Science* 245:821 (1991).

Zdsc1 polypeptides can also be used to prepare antibodies that specifically bind to Zdsc1 epitopes, peptides or polypeptides. The Zdsc1 polypeptide or a fragment thereof serves as an antigen (immunogen) to inoculate an animal and elicit an immune response. A suitable antigen would be the Zdsc1 polypeptide encoded by 5 from amino acid number 36 to amino acid number 51, also defined by SEQ ID NO:18, or a contiguous 9 amino acid residues or a fragment thereof. Antibodies generated from this immune response can be isolated and purified as described herein. Methods for preparing and isolating polyclonal and monoclonal antibodies are well known in the art. See, for example, *Current Protocols in Immunology*, Cooligan, et al. (eds.), National Institutes of Health (John Wiley and Sons, Inc., 1995); Sambrook et al., *Molecular Cloning: A Laboratory Manual*, Second Edition (Cold Spring Harbor, N.Y., 1989); and Hurrell, J. G. R., Ed., *Monoclonal Hybridoma Antibodies: Techniques and Applications* (CRC Press, Inc., Boca Raton, Fla., 1982).

Polyclonal antibodies can be generated from inoculating a variety of warm-blooded animals such as horses, cows, goats, sheep, dogs, chickens, rabbits, mice, and rats with a Zdsc1 polypeptide or a fragment thereof. The immunogenicity of a Zdsc1 polypeptide may be increased through the use of an adjuvant, such as alum (aluminum hydroxide) or Freund's complete or incomplete adjuvant. Polypeptides useful for immunization also include fusion polypeptides, such as fusions of Zdsc1 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking"

them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

Alternative techniques for generating or selecting antibodies useful herein include in vitro exposure of lymphocytes to Zdsc1 protein or peptide, and selection of antibody display libraries in phage or similar vectors (for instance, through use of immobilized or labeled Zdsc1 protein or peptide). Genes encoding polypeptides having potential Zdsc1 polypeptide binding domains can be obtained by screening random peptide libraries displayed on phage (phage display) or on bacteria, such as E. coli. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the Zdsc1 sequences disclosed herein to identify proteins which bind to Zdsc1. These "binding proteins" which interact with Zdsc1 polypeptides can be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as Zdsc1 "antagonists" to block Zdsc1 binding and signal transduction in vitro and in vivo.

Antibodies are determined to be specifically binding if: 1) they exhibit a threshold level of binding activity, and 2) they do not cross-react with related prior art polypeptide molecules. First, antibodies herein specifically bind if they bind to a Zdsc1 polypeptide, peptide or epitope with a binding affinity (Ka) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis, Scatchard, G., Ann. N.Y. Acad. Sci. 51: 660–672 (1949).

Second, antibodies are determined to specifically bind if they do not significantly cross-react with related polypeptides. Antibodies do not significantly cross-react with related polypeptide molecules, for example, if they detect Zdsc1 but not known related polypeptides using a standard Western blot analysis (Ausubel et al., ibid.). Examples of known related polypeptides are orthologs, proteins from the same species that are members of a protein family (e.g. IL-16), Zdsc1 polypeptides, and non-human Zdsc1. Moreover, antibodies may be "screened against" known related polypeptides to isolate a population that specifically binds to the inventive polypeptides. For example, antibodies raised to Zdsc1 are adsorbed to related polypeptides adhered to insoluble matrix; antibodies specific to Zdsc1 will flow through the matrix under the proper buffer conditions. Such screening allows isolation of polyclonal and monoclonal antibodies non-crossreactive to closely related polypeptides (*Antibodies: A Laboratory Manual*, Harlow and Lane (eds.), (Cold Spring Harbor Laboratory Press, 1988); *Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), (Raven Press, 1993); Getzoff et al., *Adv. in Immunol*. 43: 1–98 (1988); *Monoclonal Antibodies: Principles and Practice*, Goding, J. W. (eds.), (Academic Press Ltd., 1996); Benjamin et al., *Ann. Rev. Immunol*. 2: 67–101 (1984).

A variety of assays known to those skilled in the art can be utilized to detect antibodies which specifically bind to Zdsc1 proteins or peptides. Exemplary assays are described in detail in *Antibodies: A Laboratory Manual*, Harlow and Lane (Eds.) (Cold Spring Harbor Laboratory Press, 1988). Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant Zdsc1 protein or polypeptide.

Antibodies to Zdsc1 may be used for tagging cells that express Zdsc1; for isolating Zdsc1 by affinity purification; for diagnostic assays for determining circulating levels of Zdsc1 polypeptides; for detecting or quantitating soluble Zdsc1 as marker of underlying pathology or disease; in analytical methods employing FACS; for screening expression libraries; for generating anti-idiotypic antibodies; and as neutralizing antibodies or as antagonists to block Zdsc1 in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to Zdsc1 or fragments thereof may be used in vitro to detect denatured Zdsc1 or fragments thereof in assays, for example, Western Blots or other assays known in the art.

BIOACTIVE CONJUGATES:

Antibodies or polypeptides herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anticomplementary molecule (receptor or antigen, respectively, for instance). More specifically, Zdsc1 polypeptides or anti-Zdsc1 antibodies, or bioactive fragments or portions thereof, can be coupled to detectable or cytotoxic molecules and delivered to a mammal having cells, tissues or organs that express the anti-complementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, Pseudomonas exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin fusion proteins can be used for targeted cell or tissue inhibition or ablation (for instance, to treat cancer cells or tissues). Alternatively, if the polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the domain only fusion protein includes a complementary molecule, the anticomplementary molecule can be conjugated to a detectable or cytotoxic molecule. Such domain-complementary molecule fusion proteins thus represent a generic targeting vehicle for cell/tissue-specific delivery of generic anticomplementary-detectable/cytotoxic molecule conjugates.

The bioactive polypeptide or antibody conjugates described herein can be delivered intravenously, intraarterially or intraductally, or may be introduced locally at the intended site of action.

USES OF POLYNUCLEOTIDE/POLYPEPTIDE:

Molecules of the present invention can be used to identify and isolate receptors. For example, proteins and peptides of the present invention can be immobilized on a column and membrane preparations run over the column (Immobilized Affinity Ligand Techniques, Hermanson et al., eds., pp. 195–202 (Academic Press, San Diego, Calif., 1992,). Proteins and peptides can also be radiolabeled (*Methods in Enzymol.*, vol. 182, "Guide to Protein Purification", M. Deutscher, ed., 721–37 (Acad. Press, San Diego, 1990,) or photoaffinity labeled, Brunner et al., *Ann. Rev. Biochem.* 62:483–514 (1993) and Fedan et al., *Biochem. Pharmacol.* 33:1167–80 (1984) and specific cell-surface proteins can be identified.

GENE THERAPY:

Polynucleotides encoding Zdsc1 polypeptides are useful within gene therapy applications where it is desired to increase or inhibit Zdsc1 activity. If a mammal has a mutated or absent Zdsc1 gene, the Zdsc1 gene can be introduced into the cells of the mammal In one embodiment, a gene encoding a Zdsc polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector, Kaplitt et al., *Molec. Cell. Neurosci.* 2:320–30 (1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101 (1987); Samulski et al., *J. Virol.* 63:3822–3828 (1989).

In another embodiment, a Zdsc1 gene can be introduced in a retroviral vector, e.g., as described in Anderson et al., U.S. Pat. No. 5,399,346; Mann et al. *Cell* 33:153 (1983); Temin et al., U.S. Pat. No. 4,650,764; Temin et al., U.S. Pat. No. 4,980,289; Markowitz et al., *J. Virol.* 62:1120 (1988); Temin et al., U.S. Pat. No. 5,124,263; International Patent Publication No. WO 95/07358, published Mar. 16, 1995 by Dougherty et al.; and Kuo et al., *Blood* 82:845 (1993). Alternatively, the vector can be introduced by lipofection in vivo using liposomes. Synthetic cationic lipids can be used to prepare liposomes for in vivo transfection of a gene encoding a marker, Felgner et al., *Proc. Natl. Acad. Sci. USA* 84:7413–7 (1987); Mackey et al., *Proc. Natl. Acad. Sci. USA* 85:8027–31 (1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7 (1992); Wu et al., *J. Biol. Chem.* 263:14621–14624 (1988).

Antisense methodology can be used to inhibit Zdsc gene transcription, such as to inhibit cell proliferation in vivo. Polynucleotides that are complementary to a segment of a Zdsc1-encoding polynucleotide (e.g., a polynucleotide as set froth in SEQ ID NO:1) are designed to bind to Zdsc1-encoding mRNA and to inhibit translation of such mRNA. Such antisense polynucleotides are used to inhibit expression of Zdsc polypeptide-encoding genes in cell culture or in a subject.

The present invention also provides reagents which will find use in diagnostic applications. For example, the Zdsc1 gene, a probe comprising Zdsc1 DNA or RNA or a subsequence thereof can be used to determine if the Zdsc gene is present or if a mutation has occurred. Detectable chromosomal aberrations at the Zdsc1 gene locus include, but are not limited to, aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al, ibid.; *Marian, Chest* 108:255–65 (1995).

Transgenic mice, engineered to express the Zdsc gene, and mice that exhibit a complete absence of Zdsc gene function, referred to as "knockout mice", Snouwaert et al., *Science* 257:1083 (1992), may also be generated, Lowell et al., *Nature* 366:740–42 (1993). These mice may be employed to study the Zdsc gene and the protein encoded thereby in an in vivo system.

CHROMOSOMAL LOCALIZATION:

Radiation hybrid mapping is a somatic cell genetic technique developed for constructing high-resolution, contiguous maps of mammalian chromosomes, Cox et al., *Science* 250:245–250 (1990). Partial or full knowledge of a gene's sequence allows one to design PCR primers suitable for use with chromosomal radiation hybrid mapping panels. Radiation hybrid mapping panels are commercially available which cover the entire human genome, such as the Stanford G3 RH Panel and the GeneBridge 4 RH Panel (Research Genetics, Inc., Huntsville, Ala.). These panels enable rapid, PCR-based chromosomal localizations and ordering of genes, sequence-tagged sites (STSs), and other nonpolymorphic and polymorphic markers within a region of interest. This includes establishing directly proportional physical distances between newly discovered genes of interest and previously mapped markers. The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

Sequence tagged sites (STSs) can also be used independently for chromosomal localization. An STS is a DNA sequence that is unique in the human genome and can be used as a reference point for a particular chromosome or region of a chromosome. An STS is defined by a pair of oligonucleotide primers that are used in a polymerase chain reaction to specifically detect this site in the presence of all other genomic sequences. Since STSs are based solely on DNA sequence they can be completely described within an electronic database, for example, Database of Sequence Tagged Sites (dbSTS), GenBank, (National Center for Biological Information, National Institutes of Health, Bethesda, Md. http://www.ncbi.nlm.nih.gov), and can be searched with a gene sequence of interest for the mapping data contained within these short genomic landmark STS sequences.

For pharmaceutical use, the proteins of the present invention are formulated for parenteral, particularly intravenous or subcutaneous, delivery according to conventional methods. Intravenous administration will be by bolus injection or infusion over a typical period of one to several hours. In general, pharmaceutical formulations will include a Zdsc1 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: The Science and Practice of Pharmacy, Gennaro, ed. (Mack Publishing Co., Easton, Pa., 19th ed., 1995). Therapeutic doses will generally be in the range of 0.1 to 100 µg/kg of patient weight per day, preferably 0.5–20 µg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years.

The invention is further illustrated by the following non-limiting examples.

EXAMPLE 1

Cloning of the Murine Zdsc1 Gene

SEQ ID NO:11, an Expressed Sequence Tag (EST) was discovered in an EST data bank of an eosinophil cDNA library. The cDNA clone corresponding to the EST was discovered and sequenced to give the DNA sequence of SEQ ID NO:1. The mature protein is shown in SEQ ID NO: 3.

EXAMPLE 2

Cloning of the Human Zdsc1 Gene

SEQ ID NO:12, an EST was discovered in an EST data bank of a senescent human fibroblast cDNA library. The cDNA clone corresponding to the EST was discovered, the clone ordered from the IMAGE Consortium, Washington University School of Medicine and sequenced to give the DNA sequence of SEQ ID NO:4. The mature protein is shown in SEQ ID NO: 5.

EXAMPLE 3

Northern Blot Analysis of Zdsc1

Northern blot analysis was performed using mouse multiple tissue blot and dot blot from Clontech (Palo Alto, Calif.) and Mouse Multiple Tissue Blot from Origene (Rockville, Md.) using a 400 bp DNA probe containing the entire coding region of the Zdsc1 gene. The probe was radioactively labeled using $^{32}P$ using the MULTIPRIME® DNA labeling system (Amersham, United Kingdom) according to manufacturer's specifications. EXPRESS-HYP® solution (Clontech) was used for prehybridization and as a hybridizing solution for the Northern analysis. Hybridization of the probe on the blots took place overnight at 65° C., and the blots were than washed four times in 2×standard sodium citrate (SCC) and 0.1% sodium dodecyl sulfate (SDS) at room temperature, followed by two washes in 0.1×SSC and 0.1% SDS at 50° C. The blots were then exposed. Only one strong transcript was seen in liver for both multiple tissue blots. The dot blot showed a strong dot for liver. A faint dot for spleen and *E. coli* DNA was also seen.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polypeptide comprised of the amino acid sequence of SEQ ID NO:2, or SEQ ID NO:3.

2. A isolated polypeptide comprised of an amino acid sequence of SEQ ID NO:5.

* * * * *

SEQUENCE LISTING

<160> NUMBER OF SEQ ID NOS: 23

<210> SEQ ID NO: 1
<211> LENGTH: 365
<212> TYPE: DNA
<213> ORGANISM: Mus musculus
<220> FEATURE:
<221> NAME/KEY: CDS
<222> LOCATION: (18)...(206)

<400> SEQUENCE: 1

```
catccttcag cagcagc atg aag cta gga gcc ttc ctt ctg ttg gtg tcc        50
                   Met Lys Leu Gly Ala Phe Leu Leu Leu Val Ser
                    1               5                  10 ctc atc acc ctc agc cta gag gta cag gag ctg cag gct gca gtg aga        98
Leu Ile Thr Leu Ser Leu Glu Val Gln Glu Leu Gln Ala Ala Val Arg
            15                  20                  25 cct ctg cag ctt tta ggc acc tgt gct gag ctc tgc cgt ggt gac tgg       146
Pro Leu Gln Leu Leu Gly Thr Cys Ala Glu Leu Cys Arg Gly Asp Trp
        30                  35                  40 gac tgt ggg cca gag gaa caa tgt gtc agt att gga tgc agt cac atc       194
Asp Cys Gly Pro Glu Glu Gln Cys Val Ser Ile Gly Cys Ser His Ile
    45                  50                  55 tgt act aca aac taaaaacagc ttctacctgg aaaaaaaat gtgtctgttt            246
Cys Thr Thr Asn
 60 ggagctctgt gaccaagaaa acagttgaaa atggaggcca tgtatggaga ttacaagcag     306 cacagtggag tgggacaagg agttgtttct tttaataaat cattaatgta aaagtctca      365
```

<210> SEQ ID NO: 2
<211> LENGTH: 63
<212> TYPE: PRT
<213> ORGANISM: Mus musculus

<400> SEQUENCE: 2

```
Met Lys Leu Gly Ala Phe Leu Leu Leu Val Ser Leu Ile Thr Leu Ser
 1               5                  10                  15

Leu Glu Val Gln Glu Leu Gln Ala Ala Val Arg Pro Leu Gln Leu Leu
            20                  25                  30

Gly Thr Cys Ala Glu Leu Cys Arg Gly Asp Trp Asp Cys Gly Pro Glu
        35                  40                  45

Glu Gln Cys Val Ser Ile Gly Cys Ser His Ile Cys Thr Thr Asn
    50                  55                  60
```

<210> SEQ ID NO: 3
<211> LENGTH: 39
<212> TYPE: PRT
<213> ORGANISM: Mus musculus

<400> SEQUENCE: 3

```
Ala Val Arg Pro Leu Gln Leu Leu Gly Thr Cys Ala Glu Leu Cys Arg
 1               5                  10                  15

Gly Asp Trp Asp Cys Gly Pro Glu Glu Gln Cys Val Ser Ile Gly Cys
            20                  25                  30

Ser His Ile Cys Thr Thr Asn
        35
```

<210> SEQ ID NO: 4
<211> LENGTH: 501

```
<212> TYPE: DNA
<213> ORGANISM: Homo sapiens
<220> FEATURE:
<221> NAME/KEY: CDS
<222> LOCATION: (94)...(204)

<400> SEQUENCE: 4
gaattcggca cgaggcagca acatgaagtt ggcagccttc ctcctcctgt gatcctcatc        60
atcttcagcc tagaggtaca agagcttcag gct gca gga gac cgg ctt ttg ggt       114
                                  Ala Gly Asp Arg Leu Leu Gly
                                   1               5 acc tgc gtc gag ctc tgc aca ggt gac tgg gac tgc aac ccc gga gac        162
Thr Cys Val Glu Leu Cys Thr Gly Asp Trp Asp Cys Asn Pro Gly Asp
         10                  15                  20 cac tgt gtc agc aat ggg tgt ggc cat gag tgt gtt gca ggg                204
His Cys Val Ser Asn Gly Cys Gly His Glu Cys Val Ala Gly
         25                  30                  35 taaggacagg taaaaacacc aggccctccc tgctttctga acgttgttc agtctagatg        264 aagagttatc ttaaggatca tctttcccta agatcgtcat ccttcctgg agttcctatc       324 ttccaagatg tgactgtctg gagttccttg actaggaaga tggatgaaaa cagcaagcct      384
gtggatggag actacagggg atatgggagg cagggaagag gggttgtttc ttttaataaa      444
tcatcattgt taaaagcaaa aaaaaaaaaa aaaaaaaaa aaaatggttg cggccgc          501

<210> SEQ ID NO: 5
<211> LENGTH: 37
<212> TYPE: PRT
<213> ORGANISM: Homo sapiens

<400> SEQUENCE: 5

Ala Gly Asp Arg Leu Leu Gly Thr Cys Val Glu Leu Cys Thr Gly Asp
 1               5                  10                  15

Trp Asp Cys Asn Pro Gly Asp His Cys Val Ser Asn Gly Cys Gly His
                 20                  25                  30

Glu Cys Val Ala Gly
         35

<210> SEQ ID NO: 6
<211> LENGTH: 39
<212> TYPE: PRT
<213> ORGANISM: Homo sapiens
<220> FEATURE:
<221> NAME/KEY: VARIANT
<222> LOCATION: (0)...(0)
<223> OTHER INFORMATION: Xaa at amino acid position 1 is Ala or is
      absent; Xaa at amino acid position 2 is Val or is absent;
      Xaa at amino acid position 3 is Arg or Ala;
      Xaa at amino acid position 4 is Pro or Gly;
      Xaa at amino acid position 5 is Leu or Asp;
      Xaa at amino acid position 6 is Gln, Arg, Lys or
      Glu;
      Xaa at amino acid position 12 is Val, Ala, Ile,
      Leu, Met or Ser;
      Xaa at amino acid position 16 is Thr, Arg, Ala,
      Asn, Ser, Val, Gln, Glu, His or Lys;
      Xaa at amino acid position 22 is Asn, Gly, Asp,
      His or Ser;
      Xaa at amino acid position 24 is Ala, Arg, Asn,
      Asp, Glu, Gln, Gly, His, Lys, Pro, Ser, or Thr;
      Xaa at amino acid position 25 is Asp or Glu
      Xaa at amino acid position 26 is His, Gln Tyr or
      Glu;
      Xaa at amino acid position 30 is Ala, Arg, Asn,
      Asp, Gln, Glu, Gly His, Ile, Leu, Lys, Met, Phe,
      Ser, Thr, Tyr, or Val;
      Xaa at amino acid position 33 is Gly, Ser, Ala,
```

```
         Asn, Thr;
      Xaa at amino acid position 35 is Ala, Arg, Asn,
         Asp, Glu, Gln, Gly, His, Ile, Leu, Lys, Met Phe,
         Pro, Ser, Thr, Trp, Tyr or Val;
      Xaa at amino acid position 37 is Val or Thr;
      Xaa at amino acid position 38 is Ala or Thr; and
      Xaa at amino acid position 39 is Asn or Gly;

<400> SEQUENCE: 6

Xaa Xaa Xaa Xaa Xaa Xaa Leu Leu Gly Thr Cys Xaa Glu Leu Cys Xaa
 1               5                   10                  15

Gly Asp Trp Asp Cys Xaa Pro Xaa Xaa Xaa Cys Val Ser Xaa Gly Cys
             20                  25                  30

Xaa His Xaa Cys Xaa Xaa Xaa
         35

<210> SEQ ID NO: 7
<211> LENGTH: 40
<212> TYPE: PRT
<213> ORGANISM: Homo sapiens

<400> SEQUENCE: 7

Ile Ile Leu Ile Arg Cys Ala Met Leu Asn Pro Pro Asn Arg Cys Leu
 1               5                   10                  15

Lys Asp Thr Asp Cys Pro Gly Ile Lys Lys Cys Cys Glu Gly Ser Cys
             20                  25                  30

Gly Met Ala Cys Phe Val Pro Gln
             35                  40

<210> SEQ ID NO: 8
<211> LENGTH: 24
<212> TYPE: PRT
<213> ORGANISM: Homo sapiens

<400> SEQUENCE: 8

Met Lys Leu Gly Ala Phe Leu Leu Val Ser Leu Ile Thr Leu Ser
 1               5                   10                  15

Leu Glu Val Gln Glu Leu Gln Ala
             20

<210> SEQ ID NO: 9
<211> LENGTH: 6
<212> TYPE: PRT
<213> ORGANISM: Homo sapiens

<400> SEQUENCE: 9

Leu Gln Leu Leu Gly Thr
 1               5

<210> SEQ ID NO: 10
<211> LENGTH: 6
<212> TYPE: PRT
<213> ORGANISM: Homo sapiens

<400> SEQUENCE: 10

Asp Arg Leu Leu Gly Thr
 1               5

<210> SEQ ID NO: 11
<211> LENGTH: 371
<212> TYPE: DNA
<213> ORGANISM: Mus musculus

<400> SEQUENCE: 11
```

```
gcagcatgca agctaggagc cttccttctg ttggtgtccc tcatcaccct cagcctagag      60
gtacaggagc tgcaggctgc agtgagacct ctgcagcttt taggcacctg tgctgagctc     120
tgccgtggtg actgggactg tgggccagag gaacaatgtg tcagtattgg atgcagtcac     180
atctgtacta caaactaaaa acagcttcta cctggaaaaa aaaatgtgtc tgtttggagc     240
tctgtgacca agaaaacagt tgaaaatgga ggccatgtat ggagattaca agcagcacag     300
tggagtggga caaggagttg tttcttttaa taaatcatta atgtaaaagt caaaaaaaaa     360
aaaaaaaatt g                                                          371

<210> SEQ ID NO: 12
<211> LENGTH: 448
<212> TYPE: DNA
<213> ORGANISM: Homo sapiens

<400> SEQUENCE: 12
cagcaacatg aagttggcag ccttcctcct cctgtgatcc tcatcatctt cagcctagag      60
gtacaagagc ttcaggctgc aggagaccgg cttttgggta cctgcgtcga gctctgcaca     120
ggtgactggg actgcaaccc cggagaccac tgtgtcagca atgggtgtgg ccatgagtgt     180
gttgcagggt aaggacaggt aaaaacacca ggccctccct gctttctgaa acgttgttca     240
gtctagatga agagttatct taaggatcat cttttccctaa gatcgtcatc ccttcctgga     300
gttcctatct tccaagatgt gactgtctgg agttccttga ctaggaagat ggatgaaaac     360
agcaagcctg tggatggaga ctacagggga tatgggaggc agggaagagg ggttgtttct     420
tttaataaat catcattgtt aaaaagca                                        448

<210> SEQ ID NO: 13
<211> LENGTH: 569
<212> TYPE: DNA
<213> ORGANISM: Homo sapiens

<400> SEQUENCE: 13
gaggacccag ggtacacagg gtgggtggct attctccaga aatgtcagtt tctgggcagg      60
gcttaggtgt ctgcagtccc tagtcccacc cctggccttg cattccagct cagcgagtgg     120
aaggtataaa tttcagctgc tctcagccct gctgtgtttt tccaaagcct tccaacagca     180
acatgaagtt ggcagccttc ctcctcctgt gatcctcatc atcttcagcc tagaggtaca     240
agagcttcag gctgcaggaa gaccggcttt tgggtacctg cgtcgagctc tgcacaggtg     300
actgggactg caaccccgga gaccactgtg tcagcaatgg gtgtggccat gagtgtgttg     360
cagggtaagg acagatgaag agttatctta aggatcatct ttccctaaga tcgtcatccc     420
ttcctggagt tcctatcttc caagatgtga ctgtctggag ttccttgact aggaagatgg     480
atgaaaacag caagcctgtg gatggagact acagggggat attggaagca aggaagaggg     540
gttgttcttt taataaatca tcattgtta                                       569

<210> SEQ ID NO: 14
<211> LENGTH: 4
<212> TYPE: PRT
<213> ORGANISM: Homo sapiens

<400> SEQUENCE: 14

Ala Ala Pro Val
1
```

```
<210> SEQ ID NO: 15
<211> LENGTH: 4
<212> TYPE: PRT
<213> ORGANISM: Homo sapiens

<400> SEQUENCE: 15

Ala Ala Pro Phe
 1

<210> SEQ ID NO: 16
<211> LENGTH: 18
<212> TYPE: PRT
<213> ORGANISM: Homo sapiens

<400> SEQUENCE: 16

Thr Cys Ala Glu Leu Cys Arg Gly Asp Trp Asp Cys Gly Pro Glu Glu
 1               5                  10                  15

Gln Cys

<210> SEQ ID NO: 17
<211> LENGTH: 24
<212> TYPE: PRT
<213> ORGANISM: Homo sapiens
<220> FEATURE:
<221> NAME/KEY: VARIANT
<222> LOCATION: (0)...(0)
<223> OTHER INFORMATION: Xaa can be any amino acid residue except for
      cysteine

<400> SEQUENCE: 17

Cys Xaa Xaa Xaa Xaa Xaa Cys Xaa Xaa Xaa Xaa Xaa Cys Cys Xaa Xaa
 1               5                  10                  15

Xaa Cys Xaa Cys Xaa Xaa Xaa Cys
                20

<210> SEQ ID NO: 18
<211> LENGTH: 16
<212> TYPE: PRT
<213> ORGANISM: Homo sapiens
<220> FEATURE:
<221> NAME/KEY: VARIANT
<222> LOCATION: (0)...(0)
<223> OTHER INFORMATION: Xaa is any amino acid residue except for
      cysteine

<400> SEQUENCE: 18

Cys Xaa Xaa Xaa Xaa Xaa Xaa Xaa Xaa Xaa Xaa Cys Xaa Xaa Xaa Cys
 1               5                  10                  15

<210> SEQ ID NO: 19
<211> LENGTH: 17
<212> TYPE: PRT
<213> ORGANISM: Homo sapiens
<220> FEATURE:
<221> NAME/KEY: VARIANT
<222> LOCATION: (0)...(0)
<223> OTHER INFORMATION: Xaa is any amino acid residue except for
      cysteine.

<400> SEQUENCE: 19

Cys Xaa Xaa Xaa Xaa Xaa Xaa Cys Xaa Xaa Xaa Xaa Xaa Xaa Xaa Xaa
 1               5                  10                  15

Cys

<210> SEQ ID NO: 20
<211> LENGTH: 18
```

```
<212> TYPE: PRT
<213> ORGANISM: Homo sapiens
<220> FEATURE:
<221> NAME/KEY: VARIANT
<222> LOCATION: (0)...(0)
<223> OTHER INFORMATION: Xaa is any amino acid residue except for
      cysteine.

<400> SEQUENCE: 20

Cys Xaa Xaa Xaa Xaa Xaa Xaa Xaa Xaa Xaa Xaa Xaa Xaa Cys Xaa Xaa
 1               5                  10                  15

Xaa Cys

<210> SEQ ID NO: 21
<211> LENGTH: 14
<212> TYPE: PRT
<213> ORGANISM: Homo sapiens
<220> FEATURE:
<221> NAME/KEY: VARIANT
<222> LOCATION: (0)...(0)
<223> OTHER INFORMATION: Xaa is any amino acid residue except for
      cysteine.

<400> SEQUENCE: 21

Cys Xaa Xaa Xaa Xaa Xaa Xaa Xaa Xaa Cys Xaa Xaa Xaa Cys
 1               5                  10

<210> SEQ ID NO: 22
<211> LENGTH: 15
<212> TYPE: PRT
<213> ORGANISM: Homo sapiens
<220> FEATURE:
<221> NAME/KEY: VARIANT
<222> LOCATION: (0)...(0)
<223> OTHER INFORMATION: Xaa is any amino acid residue except for
      cysteine.

<400> SEQUENCE: 22

Cys Xaa Xaa Xaa Xaa Xaa Xaa Xaa Xaa Xaa Cys Xaa Xaa Xaa Cys
 1               5                  10                  15

<210> SEQ ID NO: 23
<211> LENGTH: 26
<212> TYPE: PRT
<213> ORGANISM: Homo sapiens
<220> FEATURE:
<221> NAME/KEY: VARIANT
<222> LOCATION: (0)...(0)
<223> OTHER INFORMATION: Xaa is any amino acid residue except for
      cysteine.

<400> SEQUENCE: 23

Cys Xaa Xaa Xaa Cys Xaa Xaa Xaa Xaa Cys Xaa Xaa Xaa Xaa Xaa
 1               5                  10                  15

Cys Xaa Xaa Xaa Xaa Cys Xaa Xaa Xaa Cys
                20                  25
```